Figure 1:
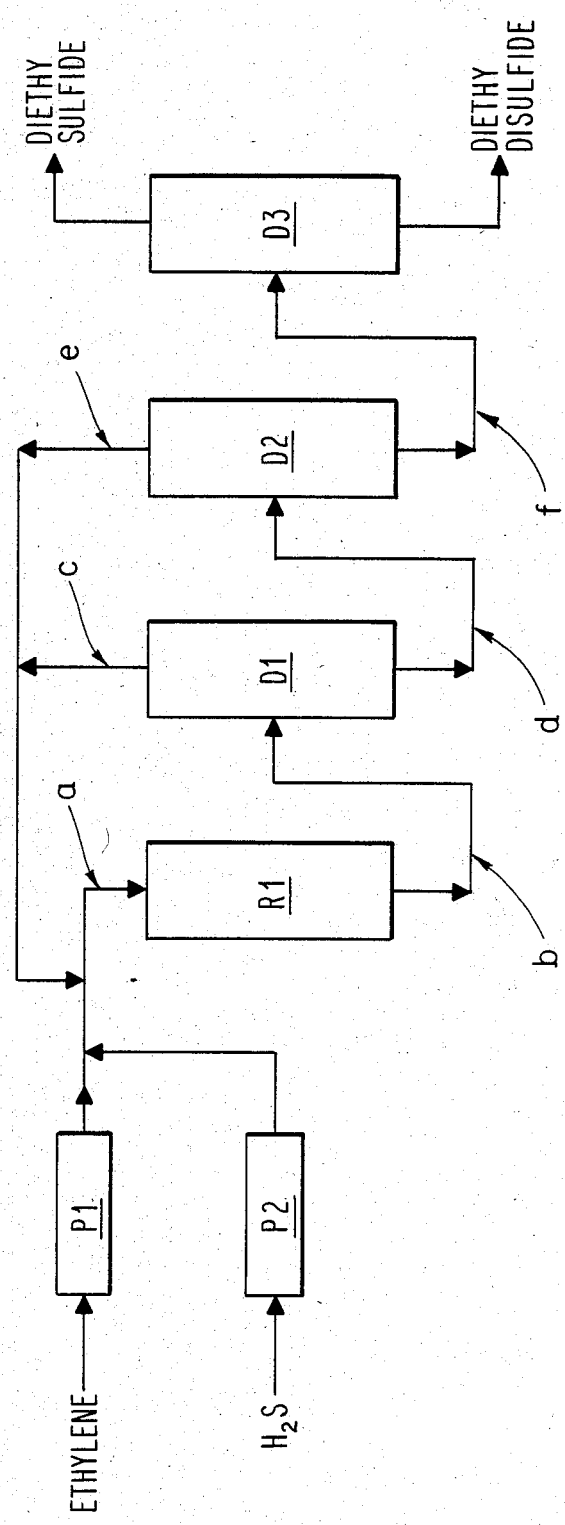

United States Patent [19]

Dzierza et al.

[11] Patent Number: 4,568,767

[45] Date of Patent: Feb. 4, 1986

[54] PROCESS FOR THE MANUFACTURE OF DIALKYL SULFIDES

[75] Inventors: Edward J. Dzierza, Philadelphia; Bernard Buchholz, Blue Bell, both of Pa.

[73] Assignee: Pennwalt Corporation, Philadelphia, Pa.

[21] Appl. No.: 333,942

[22] Filed: Dec. 23, 1981

[51] Int. Cl.$^4$ .................................. C07C 149/10
[52] U.S. Cl. ................................ 568/60; 568/59; 568/73
[58] Field of Search ................ 568/59, 60, 72, 73

[56] References Cited

U.S. PATENT DOCUMENTS 2,610,981  9/1952  Short ..................................... 568/73
3,036,133  5/1962  Goshorn et al. ..................... 568/60
3,257,464  6/1966  Buchholz et al. .................... 568/60
4,102,931  7/1978  Buchholz ............................. 568/73
4,302,605  11/1981  Buchholz et al. .................... 568/59

OTHER PUBLICATIONS

E. Reid, Organic Chemistry of Bivalent Sulfur, vol. I, p. 18, Chem. Publishing Co., Inc., New York, NY (1958).

Primary Examiner—Donald G. Daus
Assistant Examiner—Mary E. Ceperley

[57] ABSTRACT

A process is provided for the preparation of dialkyl sulfides by reacting alkenes and hydrogen sulfide at elevated temperature in the presence of a Type X, Y or L zeolite containing from about 5 to 15 percent by weight of alkali metal, expresed as Me$_2$O (where Me is an alkali metal).

13 Claims, 1 Drawing Figure

PROCESS FOR THE MANUFACTURE OF DIALKYL SULFIDES

BACKGROUND

The Prior Art

The addition of hydrogen sulfide ($H_2S$) to alkenes to produce alkyl mercaptans (Equation I) is well known. Solid catalysts such as alumina[1], ferric oxide[1], titania[1], Fuller's earth[1], silica[1], silica-alumina[1], chromia-alumina, acid clays[1], phosphoric acid on Kieselguhr or carbon[1], phosphotungstic or phosphomolybdic acid on alumina[2], sodium or potassium phosphotungstate or phosphomolybdate on alumina[2], and sodium or potassium tungstate on alumina[3] can be employed in continuous, vapor-phase processes for mercaptan manufacture. The corresponding dialkyl sulfides, formed by Equations II and III, are generally obtained as by-products in these processes.

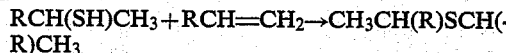

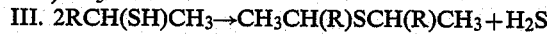

R=H or alkyl

1. E. Reid, Organic Chemistry of Bivalent Sulfur, Vol I P. 18, Chemical Publishing Co., Inc., New York, NY (1958)
2. U.S. Pat. No. 3,036,133
3. U.S. Pat. No. 3,257,464

The amount of by-product dialkyl sulfide formed can generally be controlled by varying the molar ratio of hydrogen sulfide to alkene used in the reaction mixture. Higher molar ratios of hydrogen sulfide to alkene (e.g. $H_2S$/alkene=10–20/1) favor alkyl mercaptan formation, whereas lower hydrogen sulfide to alkene molar ratios (e.g., $H_2S$/alkene=1/1) favor dialkyl sulfide formation. The phenmenon is well illustrated in the drawing accompanying U.S. Pat. No. 3,036,133. Coventional catalysts, such as those cited above, have proven efficient for the production of alkyl mercaptans from alkenes and hydrogen sulfide, where a high $H_2S$/alkene molar ratio (above about 8–10/1) is employed in the reaction mixture. However, we have discovered that these conventional catalysts suffer serious shortcomings when they are used with low molar ratios of $H_2S$/alkene in the reaction mixture to produce predominantly the dialkyl sulfides.

The major shortcoming of the prior-art catalysts stems from the fact that, at the elevated temperatures needed for reaction to occur, combined with the low $H_2S$/alkene molar feed ratios required to favor sulfide formation over mercaptan formation, appreciable tar and coke formation occurs on the surface of the catalysts. The tar and coke clog the pores of the catalyst, render its reaction-sites inaccessible to the reactants, and deactivate the catalyst after a relatively short period of operation in a continuous, vapor-phase process. The addition of an inert diluent, such as nitrogen or methane, to the feed mixture to remove heat from the reaction zone and eliminate hot spots in the catalyst bed fails to prevent the tar and coke formation. To sustain a high-production rate of dialkyl sulfides with these conventional catalysts, it is necessary to incorporate an air-regeneration cycle into the process to remove the accumulated tar and coke from the surface of the catalyst periodically and thereby restore high catalyst activity. This requirement adds appreciably to the cost of the process.

Diethyl sulfide (DES) is the preferred product of the process of this invention. DES is a well known article of commerce, being used in gas odorant mixtures and as a sulfiding agent for the post-regeneration treatment of hydrodesulfurization catalysts in petroleum refining. In the past this material has been available as a by-product from the manufacture of ethyl mercaptan. Recently, however, the demand of DES has expanded to the extent that there is a need for an efficient process by which it can be manufactured independently.

STATEMENT OF THE INVENTION

This invention is a continuous, vapor-phase process for the manufacture of $C_4$–$C_{24}$ dialkyl sulfides comprising reacting a $C_2$ to $C_{12}$ alkene with hydrogen sulfide at elevated temperature in the presence of a Type X, Y or L zeolite containing from about 5 up to 15% by weight of alkali metal, expressed as $Me_2O$. (where Me is an alkali metal).

Definitions

The zeolite (molecular sieve) catalysts used herein are synthetic alumino-silicates characterized by high uniformity, well-defined pore size, large surface area, complete crystallinity, and excellent reproducibility. Their structures are described in the Union Carbide booklet F-08 entitled, "Linde Molecular Sieve Catalysts" and D. W. Breck's, "Zeolite Molecular Sieve", John Wiley & Sons (1974). Various types are currently marketed by Linde (Union Carbide), Houdry (Air Products and Chemicals), Davison (W. R. Grace), Norton, and Akzo Chemie (Armac).

The basic structural units of synthetic zeolites are Si and Al atoms tetrahedrally coordinated with four oxygen atoms. The oxygen atoms are mutually shared between tetrahedral units contributing one of the two valence charges of each oxygen atom to each tetrahedron. Since aluminum atoms are trivalent, each $AlO_4$ is negatively charged. The charge on these units is balanced by cations, generally $Na+$ or $K+$, in the as-synthesized zeolites. These cations are exchangeable with other cations including, for example, $NH_4^+$, $Ca^{++}$, $Mg^{++}$ and the like, but the alkali metal forms at least in an amount of about 5% by weight, expressed as $Me_2O$, are required for this invention. A preferred zeolite catalyst useful for this invention contains about 13 percent by weight sodium (expressed as $Na_2O$).

Although many factors influence the catalyst activity of these zeolites, the three most important are, (1) the open framework structure with its attendant pore size, (2) the $SiO_2$:$Al_2O_3$ ratio of the framework, and (3) the cations. The large-pore zeolites having pore openings in the range of 7 to 10 Angstroms as found in the Type X, Y and L zeolites are useful for this invention. Type X has a chemical composition expressed in terms of oxide ratios of $Me_2O$:$Al_2O_3$: 2–3$SiO_2$ with a typical unit cell composition in the hydrated state of $Me_{86}[(AlO_2)_{86}(SiO_2)_{106}]264H_2O$. Type Y, on the other hand, has a composition of $Me_2O$:$Al_2O_3$:>3–6$SiO_2$. When the $SiO_2$:$Al_2O_3$ molar ratio is 4.8, the hydrated unit cellcomposition is $Me_{56}[(AlO_2)_{56}(SiO_2)_{136}]264H_2O$. Type L, more siliceous than Type X and Type Y, also has a pore size in the 7 to 10 Angstrom range.

An important building block of these zeolites is the sodalite cage, a truncated octahedron unit consisting of 24 ($Si$,$AlO_4$) units. In Type X and Type Y the sodalite cages are connected through 4 of the 8 hexagonal faces in a tetrahedral arrangement. The pores thus created are defined by a 12-member ring of oxygen atoms, approximately 7 to 9 Angstroms in size, opening into a central cavity of about 11 Angstroms in diameter.

Type L zeolite is composed of cancrinite-type cages linked by double six-ring oxygen bridges producing a structure characterized by planar 12-ring pores having an opening of about 7.1 Å. Type L has a typical oxide formula of $Me_2O:Al_2O_3:6SiO_2:H_2O$ with a typical unit cell composition in the hydrated state of $Me_9[(AlO_2)_9(SiO_2)_{27}]22H_2O$.

THE DRAWING

The drawing is a flow diagram exemplifying the process of this invention by the manufacture of DES. In the diagram, ethylene and $H_2S$ are shown to be fed continuously in a molar ratio of about 2 to 1, according to the stoichiometric requirement of the equation $2CH_2=CH_2 + H_2S \rightarrow (C_2H_5)_2S$. The reactants are vaporized and heated in preheaters (P1 and P2), mixed, and passed through a conduit (a) into the reactor (R1) containing the zeolite catalyst. Elevated temperatures, in the range of 200° to 400° C., and pressure from atmospheric to 600 psig are used to effect reaction. The crude product (b) is cooled and passed into a series of continuous distillation columns (or towers). The first column (D1) removes the low-boilers (unreacted $H_2S$ and ethylene, and methane, ethane, carbon dioxide, nitrogen or other inert gases that are used for heat removal in the process) in the overhead stream (c) and recycles them back to the reactor (R1). About 5 to 30 moles of an inert gas or mixture of gases, such as nitrogen, methane, ethane, or carbon dioxide, are needed per mole of ethylene to remove heat from the reactor for this exothermic reaction.

The bottoms stream (d) is then passed to the second distillation column (D2) where the remaining low-boilers, and the intermediate ethyl mercaptan (from equation I, supra where R=H) are removed in the overhead stream (e) and recycled, along with stream (c) to the reactor (R1). On recycling, the intermediate ethyl mercaptan is converted to DES (equations II and III, supra where R=H) over the zeolite catalyst.

The bottoms-stream (f) from the second column (D2) is passed into the final product column (D3), where high-purity DES is obtained as an overhead stream, and a minor amount of diethyl disulfide (DEDS) and high-boilers are obtained as a heavy-bottoms stream.

EXAMPLES

The following examples are intended to illustrate the process of this invention and to demonstrate the advantage of the alkali metal zeolite catalysts.

EXAMPLE 1

In the following runs, ethylene and hydrogen sulfide ($H_2S$) are reacted to produce DES. To simulate a process wherein recycled ethyl mercaptan from a process distillation column is added to the feed mixture, e.g., as shown at (a) and (e) in the flow diagram of the drawing, ethylene ($C_2H_4$), $H_2S$ and nitrogen ($N_2$=inert, heat removing diluent) are metered separately as gases, and ethyl mercaptan ($C_2H_5SH$) is pumped as a liquid, at appropriate rates to provide a continuous mixture in the desired molar ratio within the range of $1C_2H_4/3-20H_2S/2C_2H_5SH/5-17N_2$ (runs 1-14).

The above mixture is passed into an electrically-heated preheater maintained at 280±5° C. to vaporize all material and then into an electrically-heated, fixed-bed, 316 stainless steel, catalytic reactor maintained at 290°-300° C. The exit stream [(b) in the flow diagram of the drawing] is passed as a vapor by means of electrically-traced stainless steel tubing through a back-pressure control release valve and directly into the heated gas-sampling device of a gas chromatograph for analysis. The pressure in the reactor system is maintained at 235 psig, and the ethylene mole velocity is investigated at 50, 100, and 150 gram-moles of ethylene per kilogram of catalyst per 24-hour day. The catalyst for runs 1-5 is a Type Y zeolite having a sodium content of 13 percent by weight, expressed as $Na_2O$, in the form of ⅛ inch extrudate (Linde LZ-Y52 purchased from Union Carbide Corp.).

Runs 6 and 7 are carried out using the same equipment and procedure as in runs 1-4, except for the catalyst and conditions indicated in Table 1. In these runs the reactants are passed through a non-zeolitic silica-alumina catalyst wherein the alumina is 13% by weight of the alumina-silica mixture (Ketjen LA-3P purchased from Akzo Chemie). The reactor pressure is 175 psig.

Runs 8-13 are conducted using the same equipment and procedure as in runs 1-5, except for the catalyst, and conditions of Table 1. The catalyst is a non-zeolitic chromia-alumina catalyst wherein the chromia is 19% by weight of the chromia-alumina mixture (Davison Grade 909 purchased from W. R. Grace Co.) The reactor pressure is 175 psig., except for run 10 where the pressure is 200 psig.

Run 14 is carried out using the same equipment and procedure as runs 1-5 except for the catalyst, and conditions indicated in Table 1. The catalyst is a laboratory prepared material of 2% by weight of phosphotungstic acid on 98% by weight of activated alumina (Grade F-1 purchased from Alcoa). The reactor pressure is 175 psig.

Run 15 is conducted using the same equipment and procedure as in run 1-5 except that the catalyst is 2.5% by weight of potassium phosphotungstate deposited on 97.5% by weight of activated alumina (Grade F-1 purchased from Alcoa) the reactor pressure is 200 psig., and the temperature and feed ratio are according to Table 1.

The results obtained in runs 1-15 are reported in Table 1 following, wherein the use of a preferred synthetic zeolite catalyst in runs 1-5, is readily compared with the use of the conventional, non-zeolitic catalysts of runs 6-15.

TABLE 1

| | | Reaction Conditions | | | | |
|---|---|---|---|---|---|---|
| Run No. | Catalyst | $C_2H_4$ Mole Velocity | Catalyst bed temp. °C. | Molar Ratio $C_2H_4/H_2S/C_2H_5SH/N_2$ | Catalyst Use Time (Hours) | DES Production Rate lbs/1000 lbs.-cat/day |
| 1 | Na Zeolite | 50* | 291 | 1/5/2/15 | 103 | 1662 |
| 2 | Na Zeolite | 100 | 292 | 1/3/2/17 | 140 | 2717 |
| 3 | Na Zeolite | 150 | 300 | 1/5/2/15 | 146 | 4127 |
| 4 | Na Zeolite | 150 | 300 | 1/5/2/15 | 155 | 3798 |
| 5 | Na Zeolite | 150 | 290 | 1/20/2/5 | 162 | 3637 |

TABLE 1-continued

| Run No. | Catalyst | Reaction Conditions | | | Catalyst Use Time (Hours) | DES Production Rate lbs/1000 lbs.-cat/day |
| --- | --- | --- | --- | --- | --- | --- |
| | | $C_2H_4$ Mole Velocity | Catalyst bed temp. °C. | Molar Ratio $C_2H_4/H_2S/C_2H_5SH/N_2$ | | |
| 6 | Si—Alumina | 50* | 284 | 1/2/4/2 | 19 | 924 |
| 7 | Si—Alumina | 50* | 383 | 1/5/2/5 | 8 | 438 |
| 8 | Cr—Alumina | 50* | 297 | 1/2/4/6 | 17 | 2260 |
| 9 | Cr—Alumina | 50 | 281 | 1/2/4/6 | 20 | 1334 |
| 10 | Cr—Alumina | 50 | 292 | 1/2/4/6 | 28 | 856 |
| 11 | Cr—Alumina | 100* | 355 | 1/1/1/6 | 13 | 1847 |
| 12 | Cr—Alumina | 100 | 307 | 1/1/1.5/2 | 19 | 2462 |
| 13 | Cr—Alumina | 100 | 383 | 1/1/2/6 | 49 | 958 |
| 14 | Phosphotungstic acid/$Al_2O_3$ | 100* | 344 | 1/1/1/0 | 29 | 1761 |
| 15 | Potassium phosphotungstate/$Al_2O_3$ | 100* | 276 | 1/3/0/7 | 6 | 194 |

*Fresh Catalyst charge

In Table 1 above, runs 1–5 demonstrate the use of the same sodium zeolite catalyst charge for 162 operating hours with no indication at the end of the operation of deactivation. No tar or coke accumulation is observed on the surface of the catalyst on removal from the reactor.

Runs 6 and 7 demonstrate that a non-zeolitic silica-alumina catalyst is generally only about one-half as active as the sodium zeolite catalyst of runs 1–5 when the DES production rate of each is compared at the same mole velocity (50) and catalyst temperature range (284°–291° C.) but at lower reactor pressure for the non-zeolitic catalyst.

Runs 8–13 demonstrate that the non-zeolitic chromia on alumina catalyst provides high initial production rates (run 8 or runs 11 and 12) with rates falling after several hours (runs 9 and 10 or 13). On removing the catalyst from the reactor, it was observed to be heavily coked.

Run 14 is an evaluation of a phosphotungstic acid catalyst on a porous alumina support as shown in U.S. Pat. No. 3,036,133. The run demonstrates a much lower production rate (about 1000 lbs lower) for this catalyst at a higher process temperature (344° C.) compared to run 2 which is conducted at the same $C_2H_4$ mole velocity (100), at a temperature of 292° C., and at different molar reactant ratios (higher production rate is expected at higher reaction temperature). On removal of the catalyst from the reactor, it is observed to be coked, indicating eventual deactivation.

Run 15 demonstrates that potassium phosphotungstate on porous activated alumina as shown in U.S. Pat. No. 3,036,133, provides very low activity for the production of DES.

EXAMPLE 2

The runs of this example are carried out to demonstrate the selectivity of an alkali metal zeolite catalyst for the production of DES over ethyl mercaptan (runs 16–21) compared to an acid zeolite catalyst (runs 22–28). Ethylene and $H_2S$ are reacted at selected ethylene mole velocities, catalyst bed temperatures, reactor pressures and feed molar ratios. Runs 16–21 employ the sodium zeolite catalyst of runs 1–5 while runs 19–20 and 28 use recycled ethyl mercaptan as described in Example 1. All runs of Example 2 are conducted with the same equipment as Example 1. Runs 22–28 employ an acid (protonated) zeolite (Linde LZ-Y62) prepared by exchanging the sodium cations on the Linde LZ-Y52 zeolite, used in runs 1–5 and 16–21, with ammonium cations and calcining the resulting zeolite to remove ammonia and leave essentially a protonated zeolite containing only about 2.5 percent by weight of sodium expressed as $Na_2O$.

The results obtained for runs 16–28 are reported in Table 2 following.

TABLE 2

| Run No. | Catalyst | Reaction Conditions | | | | Catalyst Use Time Hours | Production Rate lbs/1000 lbs. cat/day | |
| --- | --- | --- | --- | --- | --- | --- | --- | --- |
| | | $C_2H_4$ Mole Velocity | Catalyst Bed. Temp. °C. | Pressure Psig. | Molar Ratio $C_2H_4/H_2S/C_2H_5SH/N_2$ | | $C_2H_5SH$ | DES |
| 16 | Na Zeolite | 88* | 288 | 235 | 1/13/0/0 | 15 | 1321 | 1074 |
| 17 | " | 88 | 303 | 235 | 1/8/0/0 | 23 | 1722 | 1509 |
| 18 | " | 88 | 297 | 235 | 1/8/0/2 | 42 | 1368 | 1811 |
| 19 | " | 88 | 283 | 235 | 1/8/1/2 | 48 | — | 1990 |
| 20 | " | 100* | 294 | 235 | 1/5/2/15 | 119 | — | 2571 |
| 21 | " | 100 | 292 | 235 | 1/3/2/17 | 140 | — | 2717 |
| 22 | H+ Zeolite | 50* | 304 | 120 | 1/10/0/5 | 30 | 1154 | 53 |
| 23 | " | 50 | 305 | 120 | 1/10/0/0 | 34 | 1552 | 165 |
| 24 | " | 50 | 302 | 120 | 1/6/0/0 | 42 | 1334 | 287 |
| 25 | " | 100* | 298 | 175 | 1/6/0/0 | 11 | 3173 | 610 |
| 26 | " | 100 | 296 | 175 | 1/3/0/0 | 15 | 2947 | 1049 |
| 27 | " | 100 | 298 | 175 | 1/2/0/0 | 22 | 1432 | 700 |
| 28 | " | 100* | 377 | 120 | 1/3/10/10 | 26 | — | 1157 |

*Fresh catalyst charge
— (dash) indicates no measurement of recycle $C_2H_5SH$ made.

The data in the above Table 2 (runs 16–18) show that when ethylene and $H_2S$ are reacted in a single pass over the alkali metal zeolite catalyst, about equal quantities of ethyl mercaptan and DES are formed, even when high molar ratios of H$_2$S/ethylene (8/1 to 13/1) are used. On the other hand when ethylene and H$_2$S are passed over the protonated zeolite catalyst (runs 22-27) with high molar ratios of H$_2$S/ethylene (6/1 to 10/1), the formation of ethyl mercaptan is greatly favored over the formation of DES. Runs 19-21 demonstrate that greater production rates are obtained with recycled mercaptan in the process of this invention. In run 28, ethylene and H$_2$S were reacted in the same equipment and under similar conditions as the reaction conducted in run 2 of Table 1. At the same ethylene velocity, a higher reaction temperature, the same reactant ratio of 1/3 and a greater mole ratio of recycled mercaptan, as compared to run 2, the DES production rate in run 28 is less than one-half the production rate in run 2 (2717 lbs.) or 1157 lbs. per 1000 lbs of catalyst per day. The acid (protonated) zeolite of run 28, when removed from the reactor after the run, is observed to be heavily coked after 26 hours operation.

Discussion-Generic

The continuous, vapor-phase process for manufacture of C$_4$ to C$_{24}$ dialkyl sulfides, preferably diethyl sulfide, as disclosed herein, requires the reaction of a C$_2$-C$_{12}$ alkene and hydrogen sulfide in the presence of an alkali metal zeolite containing at least 5% by weight of an alkali metal, expressed as Me$_2$O. By-product alkyl mercaptan can be recycled in the process to provide higher conversions and yields.

The Reactants

The alkenes that are useful for this invention are those straight or branch chained compounds having from 2 to 12 carbon atoms, e.g., ethylene, propylene, butene, pentene, heptene, octene, decene, dodecene and their respective mono-olefinic isomers. The olefinic double-bond is located either in the alpha position or internally to produce the corresponding dialkyl sulfide. The preferred alkene is ethylene.

Hydrogen sulfide can be obtained from any source providing a reasonably pure product.

The molar ratio of fresh alkene and fresh H$_2$S fed to the reactor ranges from about 5:1 to 1:5 preferably from 2.5:1 to 1:2.5, most preferably near the stoichiometric ratio of 2:1. The molar ratio of the alkene and H$_2$S, when combining the fresh feed with recycle feed, i.e., alkene, H$_2$S, alkyl mercaptan, etc., can, of course, be in excess of the above and will usually be a molar excess of H$_2$S over alkene which may be as high as 20:1.

The Catalysts

The catalysts of this invention have been defined hereinbefore under *Definitions* and are those Type X,Y and L zeolites containing at least about 5 up to about 15 percent of an alkali metal, expressed as Me$_2$O the secondary cations, if any, may, for example, be ammonium, a different alkali metal or an alkaline earth metal. The preferred catalyst is the Type Y zeolite in which the cation is sodium at a weight percent, based on the weight of the zeolite, of from about 10 to about 15 (expressed as Na$_2$O). An example of a commercially available zeolite of this type is Linde LZ-Y52 sold by Union Carbide Corporation.

Reaction Conditions

The rate of feed of reactant mix into the reactor is controlled by the rate at which fresh alkene is passed over the catalyst and this rate ranges from about 20 to about 300 gram-moles, preferably about 50 to about 200 gram-moles, of alkene per kilogram of catalyst per 24 hours.

The temperature of this process is controlled by the temperature of the catalyst bed which can range from about 200° to about 400° C., preferably from about 235° to about 350° C. Pressures in the process range from atmospheric to about 600 psig, preferably from about 50 to about 450 psig.

An inert gas is usually employed as a part of the feed mixture to provide sufficient heat removal from the catalyst zone. The inert gas may, for example, be nitrogen, methane, ethane, propane, butane, carbon dioxide, or any non-reactive gas or mixture of gases that does not adversely affect the reaction to produce the desired dialkyl sulfide. The molar ratio of the inert gas, or mixture of inert gases, used to remove heat from the exothermic reaction, to the fresh alkene feed is that required to maintain the catalyst bed temperature within the required range, generally between about 5:1 and 30:1, preferably between about 8:1 and 15:1. The inert gases are usually recycled to the system after cooling and need not be replenished continuously.

In the process of this invention, production rates in the commercially attractive range of 3600 to about 4100 pounds of DES per 1000 pounds of catalyst per 24 hour day have been demonstrated as quite easily attained using the following operating conditions:

Ethylene mole velocity=150 pound-moles/1000 pounds of catalyst per day

Catalyst bed temperature=290°-300° C.

Reactor pressure=235 psig.

Molar ratio C$_2$H$_4$/H$_2$S/C$_2$H$_5$SH/N$_2$=1/5-20/2/-15-5

The process of this invention is an advancement over the prior art processes in that dialkyl sulfides can be manufactured without the co-production of large amounts of the corresponding alkyl mercaptans. In the preparation of DES with this process, the intermediate ethyl mercaptan is generally totally recycled to produce DES in high over-all yield from ethylene and H$_2$S, although some of the ethyl mercaptan can be separated and collected as a by-product, if desired.

Another advantage of this process is that high dialkyl sulfide production rates can be sustained over long periods of operation since the catalysts used do not form tars and coke by-products, as do conventional non-zeolitic catalysts and protonated zeolite catalysts, and do not require periodic air-regenerations of the catalyst to remove tars and coke.

We claim:

1. A continuous, vapor-phase reaction for preparing C$_4$-C$_{24}$ dialkyl sulfides which comprises contacting a feed of C$_2$-C$_{12}$ alkene and hydrogen sulfide at a temperature in the range of about 235° to about 400° C. with a Type X, Y or L zeolite containing from about 5 up to 15 percent by weight alkali metal, expressed as Me$_2$O, where Me is an alkali metal.

2. The process of claim 1 wherein the crude reaction product of said process comprises a mixture of alkyl mercaptan and the corresponding dialkyl sulfide, and said alkyl mercaptan is separated and recycled as part of said feed.

3. The process of claim 2 wherein the pressure of said reaction ranges from about atmospheric to about 600 psig.

4. The process of claim 2 wherein the molar ratio of hydrogen sulfide to alkene exclusive of recycled product is from about 5:1 to about 1:5.

5. The process of claim 2 wherein the rate at which the alkene contacts said zeolite ranges from about 20 to about 300 gram-moles of alkene per kilogram of zeolite per 24 hours.

6. The process of claim 2 wherein an inert gas is a part of said feed and is continuously recycled in the process to remove exothermic heat of reaction.

7. The process of claim 2 wherein the zeolite is Type Y containing from about 10 up to 15 percent by weight alkali metal.

8. The process of claim 7 wherein the alkali metal is sodium or potassium.

9. The process of claim 8 wherein the alkene is ethylene.

10. The process of claim 9 wherein the elevated temperature is in the range of from about 235° to about 350° C. and the pressure of said reaction ranges from about 50 to about 450 psig.

11. The process of claim 10 wherein the alkene contacts said zeolite at a rate in the range of from about 50 to about 200 gram-moles per kilogram of zeolite per 24 hours.

12. The process of claim 11 wherein the alkene and hydrogen sulfide are continuously fed to the reaction at a molar ratio, exclusive of recycled product, of about 2:1, and said crude reaction product, after separation of alkyl mercaptan, is continuously distilled to provide a dialkyl sulfide having a purity of at least about 95 percent.

13. The process of claim 11 or 12 wherein an inert gas is a part of said feed and is continuously recycled in the process to remove exothermic heat of reaction.

* * * * *